(12) United States Patent
Kizuka

(10) Patent No.: US 11,116,633 B2
(45) Date of Patent: Sep. 14, 2021

(54) OPPOSING DISK DEVICE FOR GRASPING CARDIAC VALVE TISSUE

(71) Applicant: Evalve, Inc., Santa Clara, CA (US)

(72) Inventor: Koji J. Kizuka, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 252 days.

(21) Appl. No.: 16/519,635

(22) Filed: Jul. 23, 2019

(65) Prior Publication Data
US 2019/0343630 A1 Nov. 14, 2019

Related U.S. Application Data

(63) Continuation of application No. 15/349,288, filed on Nov. 11, 2016, now Pat. No. 10,398,553.

(51) Int. Cl.
A61F 2/24 (2006.01)
A61B 17/122 (2006.01)
(Continued)

(52) U.S. Cl.
CPC .......... *A61F 2/2445* (2013.01); *A61B 17/122* (2013.01); *A61F 2/246* (2013.01); *A61F 2/2466* (2013.01); *A61B 17/1227* (2013.01); *A61B 17/1285* (2013.01); *A61B 2017/00243* (2013.01); *A61B 2017/00783* (2013.01); *A61B 2017/00876* (2013.01); *A61F 2220/0008* (2013.01); *A61F 2230/001* (2013.01); *A61F 2230/0006* (2013.01); *A61F 2230/0078* (2013.01)

(58) Field of Classification Search
CPC ........ A61F 2/24; A61F 2/2415; A61F 2/2418; A61F 2/2445
See application file for complete search history.

(56) References Cited

U.S. PATENT DOCUMENTS 3,296,668 A 1/1967 Aiken
3,675,639 A 7/1972 Cimber
(Continued)

FOREIGN PATENT DOCUMENTS

CN 102770080 11/2012
DE 3504292 7/1986
(Continued)

OTHER PUBLICATIONS

Alfieri et al., "An Effective Technique to Correct Anterior Mitral Leaflet Prolapse," J. Card Surg., 14:468-470 (1999).
(Continued)

*Primary Examiner* — Jason-Dennis N Stewart
(74) *Attorney, Agent, or Firm* — Workman Nydegger

(57) ABSTRACT

The present disclosure relates to repair devices and methods for repair of regurgitant tricuspid valves. A repair method includes positioning a repair device at a tricuspid valve in a collapsed configuration. The repair device includes a proximal grasping assembly movable between a first position and a second position and a distal grasping assembly movable between a third position and a fourth position. An actuator rod operatively connected to each of the proximal grasping assembly and the distal grasping assembly so that distal movement of the actuator rod simultaneously moves the proximal grasping assembly proximally and the distal grasping assembly distally.

20 Claims, 12 Drawing Sheets

(51) Int. Cl.
  *A61B 17/128*   (2006.01)
  *A61B 17/00*    (2006.01)

(56) References Cited

U.S. PATENT DOCUMENTS

| | | |
|---|---|---|
| 3,874,388 A | 4/1975 | King et al. |
| 4,007,743 A | 2/1977 | Blake |
| 4,531,522 A | 7/1985 | Bedi et al. |
| 4,686,965 A | 8/1987 | Bonnet et al. |
| 5,171,259 A | 12/1992 | Inoue |
| 5,342,393 A | 8/1994 | Stack |
| 5,350,399 A | 9/1994 | Erlebacher et al. |
| 5,391,182 A | 2/1995 | Chin |
| 5,520,701 A | 5/1996 | Lerch |
| 5,575,802 A | 11/1996 | McQuilkin et al. |
| 5,620,452 A | 4/1997 | Yoon |
| 5,649,937 A | 7/1997 | Bito et al. |
| 5,718,725 A | 2/1998 | Sterman et al. |
| 5,769,812 A | 6/1998 | Stevens et al. |
| 5,861,003 A | 1/1999 | Latson et al. |
| 5,928,224 A | 7/1999 | Laufer |
| 5,972,030 A | 10/1999 | Garrison et al. |
| 6,063,106 A | 5/2000 | Gibson |
| 6,117,159 A | 9/2000 | Huebsch et al. |
| 6,165,183 A | 12/2000 | Kuehn et al. |
| 6,306,133 B1 | 10/2001 | Tu et al. |
| 6,312,447 B1 | 11/2001 | Grimes |
| 6,461,366 B1 | 10/2002 | Seguin |
| 6,485,489 B2 | 11/2002 | Teirstein et al. |
| 6,508,828 B1 | 1/2003 | Akerfeldt et al. |
| 6,575,971 B2 | 6/2003 | Hauck et al. |
| 6,616,684 B1 | 9/2003 | Vidlund et al. |
| 6,626,899 B2 | 9/2003 | Houser et al. |
| 6,629,534 B1 | 10/2003 | St. Goar et al. |
| 6,695,866 B1 | 2/2004 | Kuehn et al. |
| 6,702,825 B2 | 3/2004 | Frazier et al. |
| 6,875,224 B2 | 4/2005 | Grimes |
| 6,926,715 B1 | 8/2005 | Hauck et al. |
| 7,291,168 B2 | 11/2007 | Macoviak et al. |
| 8,523,881 B2 | 9/2013 | Cabiri et al. |
| 10,398,553 B2 | 9/2019 | Kizuka |
| 2001/0002445 A1 | 5/2001 | Vesely |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2002/0013571 A1 | 1/2002 | Goldfarb et al. |
| 2002/0055775 A1 | 5/2002 | Carpentier et al. |
| 2002/0087148 A1 | 7/2002 | Brock et al. |
| 2002/0087169 A1 | 7/2002 | Brock et al. |
| 2002/0147456 A1 | 10/2002 | Diduch et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0074012 A1 | 4/2003 | Nguyen et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0208231 A1 | 11/2003 | Williamson, IV et al. |
| 2004/0002719 A1 | 1/2004 | Oz et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0133062 A1 | 7/2004 | Pai et al. |
| 2004/0133192 A1 | 7/2004 | Houser et al. |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0153144 A1 | 8/2004 | Seguin |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0249453 A1 | 12/2004 | Cartledge et al. |
| 2005/0004583 A1 | 1/2005 | Oz et al. |
| 2005/0021056 A1 | 1/2005 | St. Goer et al. |
| 2005/0021057 A1 | 1/2005 | St. Goer et al. |
| 2005/0033446 A1 | 2/2005 | Deem et al. |
| 2005/0038508 A1 | 2/2005 | Gabbay |
| 2005/0085903 A1 | 4/2005 | Lau |
| 2005/0143809 A1 | 6/2005 | Salahieh et al. |
| 2005/0149014 A1 | 7/2005 | Hauck et al. |
| 2005/0159810 A1 | 7/2005 | Filsoufi |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0267493 A1 | 12/2005 | Schreck et al. |
| 2006/0004247 A1 | 1/2006 | Kute et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0195012 A1 | 8/2006 | Mortier et al. |
| 2006/0252984 A1 | 11/2006 | Randert et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2008/0195126 A1 | 8/2008 | Solem |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0276039 A1 | 11/2009 | Meretei |
| 2010/0016958 A1 | 1/2010 | St. Goer et al. |
| 2010/0022823 A1 | 1/2010 | Goldfarb et al. |
| 2010/0044410 A1 | 2/2010 | Argentine et al. |
| 2011/0264208 A1 | 10/2011 | Duffy et al. |

(56) References Cited

U.S. PATENT DOCUMENTS

| | | |
|---|---|---|
| 2012/0016464 A1 | 1/2012 | Seguin |
| 2012/0022640 A1 | 1/2012 | Gross et al. |
| 2012/0065464 A1 | 3/2012 | Ellis et al. |
| 2012/0316639 A1 | 12/2012 | Kleinschrodt |
| 2012/0330348 A1 | 12/2012 | Strauss et al. |
| 2013/0066342 A1 | 3/2013 | Dell et al. |
| 2014/0324164 A1 | 10/2014 | Gross et al. |
| 2014/0358224 A1 | 12/2014 | Tegels et al. |
| 2015/0112430 A1 | 4/2015 | Creaven et al. |
| 2015/0257879 A1 | 9/2015 | Börtlein et al. |
| 2016/0174979 A1 | 6/2016 | Wei |
| 2017/0042678 A1 | 2/2017 | Ganesan et al. |
| 2018/0021133 A1 | 1/2018 | Barbarino |
| 2018/0021134 A1 | 1/2018 | McNiven et al. |
| 2018/0028215 A1 | 2/2018 | Cohen |
| 2018/0133010 A1 | 5/2018 | Kizuka |
| 2018/0360457 A1 | 12/2018 | Ellis et al. |
| 2019/0274831 A1 | 9/2019 | Prabhu |

FOREIGN PATENT DOCUMENTS

| | | |
|---|---|---|
| EP | 0179562 | 7/1989 |
| EP | 1674040 | 6/2006 |
| EP | 2537487 | 12/2012 |
| GB | 1598111 | 9/1981 |
| JP | 2006528911 | 12/2006 |
| JP | 2013516244 | 5/2013 |
| JP | 2014523274 | 9/2014 |
| WO | WO 1981000668 | 3/1981 |
| WO | WO 1994018893 | 9/1994 |
| WO | WO 1996020655 | 7/1996 |
| WO | WO 1996022735 | 8/1996 |
| WO | WO 1997025927 | 7/1997 |
| WO | WO 1997038748 | 10/1997 |
| WO | WO 1998007375 | 2/1998 |
| WO | WO 1998032382 | 7/1998 |
| WO | WO 2000044313 | 8/2000 |
| WO | WO 2001000114 | 1/2001 |
| WO | WO 2001026557 | 4/2001 |
| WO | WO 2001028432 | 4/2001 |
| WO | WO 2001054618 | 8/2001 |
| WO | WO 2002001999 | 1/2002 |
| WO | WO 2002003892 | 1/2002 |
| WO | WO 2002034167 | 5/2002 |
| WO | WO 2003001893 | 1/2003 |
| WO | WO 2003020179 | 3/2003 |
| WO | WO 2003037171 | 5/2003 |
| WO | WO 2003049619 | 6/2003 |
| WO | WO 2003105667 | 12/2003 |
| WO | WO 2004012583 | 2/2004 |
| WO | WO 2004012789 | 2/2004 |
| WO | WO 2004014282 | 2/2004 |
| WO | WO 2004019811 | 3/2004 |
| WO | WO 2004030570 | 4/2004 |
| WO | WO 2004045370 | 6/2004 |
| WO | WO 2004045378 | 6/2004 |
| WO | WO 2004045463 | 6/2004 |
| WO | WO 2005018507 | 3/2005 |
| WO | WO 2005032421 | 4/2005 |
| WO | WO 2005062931 | 7/2005 |
| WO | WO 2005112792 | 12/2005 |
| WO | WO 2006037073 | 4/2006 |
| WO | WO 2006105008 | 10/2006 |
| WO | WO 2006105009 | 10/2006 |
| WO | WO 2006115876 | 11/2006 |
| WO | WO 2008103722 | 8/2008 |
| WO | WO 2010121076 | 10/2010 |
| WO | WO 2012061809 | 5/2012 |
| WO | WO 2012103173 | 8/2012 |
| WO | WO 2015057407 | 4/2015 |
| WO | WO 2016144708 | 9/2016 |
| WO | WO 2016150806 | 9/2016 |
| WO | WO 2018089618 | 5/2018 |

OTHER PUBLICATIONS

Alfieri et al., "Novel Suture Device for Beating Heart Mitral Leaflet Approximation," Annals of Thoracic Surgery, 74:1488-1493 (2002).
Alfieri et al., "The edge to edge technique," The European Association for Cardio-Thoracic Surgery 14th Annual Meeting, Oct. 7-11, 2000, Book of Proceedings.
Chinese Office Action issued in Chinese Application No. 200980158707.2 dated Sep. 9, 2013.
Communication dated Apr. 16, 2018 from the European Patent Office in counterpart European application No. 04752603.3.
Extended European Search Report, dated Oct. 17, 2014, issued in European Patent Application No. 06751584.1.
Morales et al., "Development of an Off Bypass Mitral Valve Repair," The Heart Surgery Forum #1999-4693, 2(2):115-120 (1999).
Patel et al., #57 Epicardial Atrial Defibrillation: Novel Treatment of Postoperative Atrial Fibrillation, 2003 STS Presentation, [Abstract Only].
Tibayan et al., #59 Annular Geometric Remodeling in Chronic Ischemic Mitral Regurgitation, 2003 STS Presentation, [Abstract Only].
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 15/349,288, Jan. 14, 2019, Office Action.
U.S. Appl. No. 15/349,288, May 2, 2019, Notice of Allowance.
Bhudia et al., "Edge-to-Edge (Alfieri) Mitral Repair: Results in Diverse Clinical Settings," Ann Thorac Surg, 77:1598-1606 (2004).

OPPOSING DISK DEVICE FOR GRASPING CARDIAC VALVE TISSUE

CROSS-REFERENCE TO RELATED APPLICATIONS

This application is a continuation of U.S. patent application Ser. No. 15/349,288, filed Nov. 11, 2016, the entire contents of which are incorporated herein by this reference.

BACKGROUND

The tricuspid valve controls blood flow from the right atrium to the right ventricle of the heart, preventing blood from flowing backwards from the right ventricle into the right atrium so that it is instead forced through the pulmonary valve and into the pulmonary arteries for delivery to the lungs. A properly functioning tricuspid valve opens and closes to enable blood flow in one direction. However, in some circumstances the tricuspid valve is unable to close properly, allowing blood to regurgitate back into the atrium. Such regurgitation can result in shortness of breath, fatigue, heart arrhythmias, and even heart failure.

Tricuspid valve regurgitation has several causes. Functional tricuspid valve regurgitation (FTR) is characterized by structurally normal tricuspid valve leaflets that are nevertheless unable to properly coapt with one another to close properly due to other structural deformations of surrounding heart structures. Often, the right ventricle is dilated as a result of pulmonary hypertension or an abnormal heart muscle condition (cardiomyopathy).

Other causes of tricuspid valve regurgitation are related to defects of the tricuspid valve leaflets, tricuspid valve annulus, or other tricuspid valve tissues. In some circumstances, tricuspid valve regurgitation is a result of infective endocarditis, blunt chest trauma, rheumatic fever, Marfan syndrome, carcinoid syndrome, or congenital defects to the structure of the heart. Tricuspid valve conditions are also often associated with problems related to the left side of the heart, such as mitral valve regurgitation.

Tricuspid valve regurgitation is often treated by replacing the tricuspid valve with a replacement valve implant or by repairing the valve through an interventional procedure. However, issues can arise related to deployment and effectiveness of various treatment options. For instance, properly positioning and aligning a repair device with respect to the tricuspid valve can be difficult, particularly considering that the valve leaflets and other structures are continuously moving within the dynamic cardiac environment.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices and methods for repairing tissue, such as tissue of a malfunctioning cardiac valve, including a regurgitant tricuspid valve. In some embodiments, a method for repairing a targeted cardiac valve includes positioning and/or delivering a repair device, which is passable between a collapsed configuration and an expanded configuration, at a targeted cardiac valve, such as a regurgitant tricuspid valve. In some embodiments, the repair device includes a proximal disk, a distal disk spaced apart from the proximal disk so as to define a grasping space therebetween for grasping cardiac valve tissue, and a neck section joining the proximal disk and the distal disk, the neck section having a diameter that is smaller than a diameter of the proximal disk and the distal disk.

In certain embodiments, the distal disk is then deployed on a first side of the targeted cardiac valve by passing the distal disk from the collapsed configuration to the expanded configuration. The proximal disk is then deployed on a second side of the targeted cardiac valve by passing the proximal disk from the collapsed configuration to the expanded configuration so as to grasp the targeted cardiac valve tissue (e.g., tricuspid valve leaflets) between the deployed distal disk and the deployed proximal disk.

In some embodiments, deployment of the proximal disk simultaneously captures the three leaflets of the tricuspid valve between the proximal disk and the distal disk. In some embodiments, the grasping space is sized and shaped to conform to an anatomical shape of the targeted tricuspid valve leaflets. In certain embodiments, the repair device includes a plurality of grip elements configured to enhance engagement of the repair device with the targeted cardiac valve tissue upon deployment of the repair device. In some embodiments, the grip elements are disposed on the proximal disk at an area of the proximal disk facing the distal disk, and are disposed on the distal disk at an area of the distal disk facing the proximal disk. In some embodiments, the repair device includes a wireframe structure formed from a superelastic/shape-memory material, such as nitinol.

In some embodiments, the repair device is delivered to a targeted cardiac valve through a transjugular approach. In some embodiments, prior to deployment, the distal disk and the proximal disk are maintained in the collapsed configuration by a sheath, and wherein the distal disk and the proximal disk are passed to respective expanded configurations by unsheathing the distal section and the proximal section. In some embodiments, the distal disk is deployed on a ventricular side of the targeted valve, and wherein the proximal disk is deployed on an atrial side of the targeted valve.

In some embodiments, an interventional device configured for repair of a regurgitant tricuspid valve includes a proximal disk passable between a collapsed configuration and an expanded configuration; a distal disk passable between a collapsed configuration and an expanded configuration, the distal disk being spaced apart from the proximal disk so as to define a grasping space therebetween for grasping tricuspid valve leaflets when the proximal disk and the distal disk are in expanded configurations and are deployed at a tricuspid valve; and a neck section joining the proximal disk and the distal disk, the neck section having a diameter that is smaller than a diameter of the proximal disk and the distal disk.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

At least some of the embodiments described herein are directed to devices and methods for repairing a malfunctioning cardiac valve, such as a regurgitant tricuspid valve. Some embodiments are directed to devices and methods configured to provide repair of a regurgitant tricuspid valve utilizing an opposing disk repair device configured for grasping and fixing the three leaflets of the tricuspid valve together in a desired configuration to improve valve closure and minimize or eliminate regurgitation at the tricuspid valve.

Although many of the examples illustrated and described herein are directed to tricuspid valve regurgitation, it will be understood that the principles, features, and components described herein may also be applied in other applications, such as repair of other heart valves, or use in other interventional procedures or treatment applications.

Figure 1:
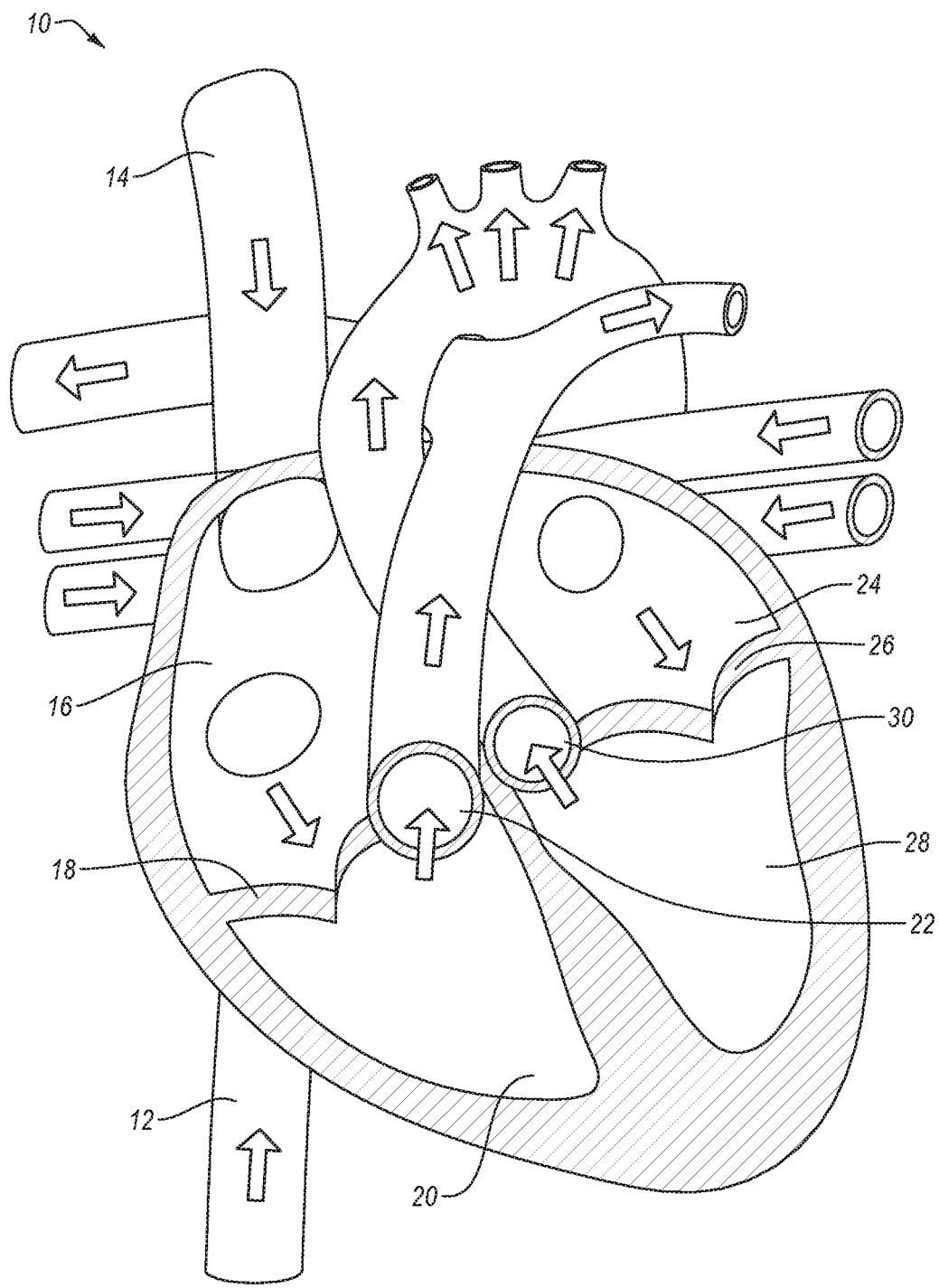
FIG. 1 illustrates a human heart showing normal blood flow paths.

FIG. 1 illustrates a cross-sectional view of a heart 10 showing a normal blood flow path through the heart. Deoxygenated blood enters the right atrium 16 through the superior vena cava 14 and superior vena cava 12. During diastole, suction from expansion of the right ventricle 20 and pressure from contraction of the right atrium 16 forces blood from the right atrium 16 across the tricuspid valve 18 and into the right ventricle 20. During ventricular systole, blood is then forced from the right ventricle 20 through the pulmonary valve 22 and into the pulmonary arteries for delivery to the lungs. In a normally functioning heart, the tricuspid valve 18 closes during systole to prevent backwards movement of blood from the right ventricle 20 back into the right atrium 16. When a tricuspid valve is not functioning properly, it may fail to fully close such that some of the blood passes back across the tricuspid valve 18 and into the right atrium 16, rather than through the pulmonary valve 22.

Oxygenated blood returning from the lungs enters the left atrium 24, where it is then passed through the mitral valve 26 and into the left ventricle 28. During ventricular systole, the blood is then passed from the left ventricle through the aortic valve for delivery throughout the body. Similar to the right side of the heart, failure of the mitral valve 26 to fully close during ventricular systole leads to regurgitation of blood from the left ventricle 28 back into the left atrium 24. In some circumstances, problems related to mitral valve regurgitation or other issues with the left side of the heart also cause or are associated with structural issues on the right side of the heart, such as tricuspid valve regurgitation.

Figure 2:
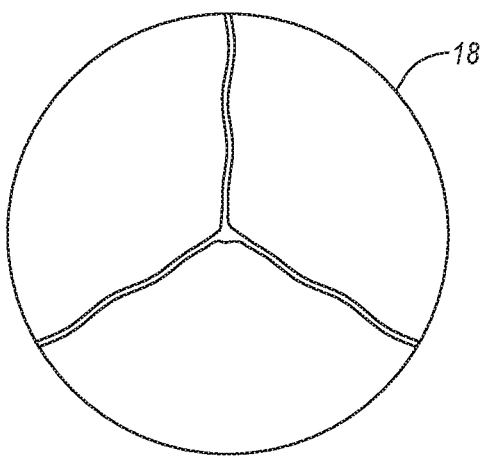
FIG. 2 illustrates a superior view of a normally functioning tricuspid valve in a closed position.
Figure 3:
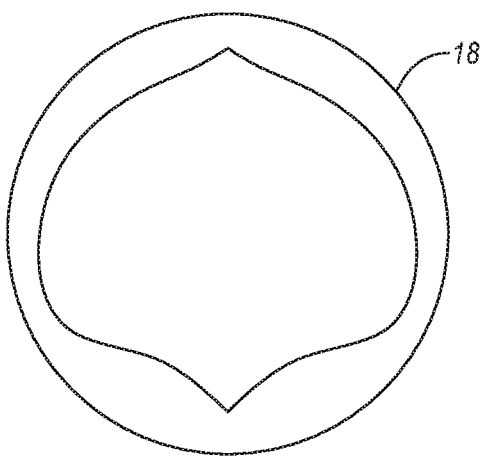
FIG. 3 illustrates a superior view of a tricuspid valve in an open position.
Figure 4:
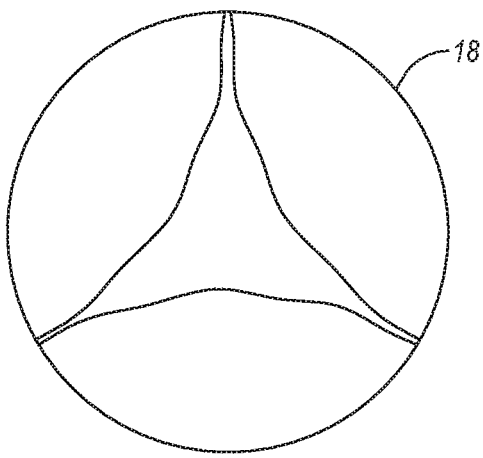
FIG. 4 illustrates a superior view of a malfunctioning tricuspid valve unable to properly close.

FIGS. 2-4 illustrate superior views of a tricuspid valve 18 in various states and positions. FIG. 2 illustrates a properly functioning tricuspid valve 18 in a closed position. A properly functioning tricuspid valve 18 takes this form during ventricular systole in order to block backflow of blood. As shown, when in the closed position, the three leaflets of the tricuspid valve 18 coapt to fully close the valve. FIG. 3 illustrates a properly functioning tricuspid valve 18 in an open position. When open, the leaflets of the tricuspid valve 18 extend downward into the right ventricle so that passage of blood through the tricuspid valve 18 is provided.

FIG. 4 illustrates a defective tricuspid valve 18 during ventricular systole. In contrast to the properly closed tricuspid valve of FIG. 2, the leaflets of the defective tricuspid valve are unable to fully coapt, leaving a passage through which regurgitant blood may pass. The inability to fully close may be due to defects to the leaflets themselves, or to defects to other structures of the heart which deform the tricuspid valve annulus or stretch the chordae tendineae, for example.

Figure 5:
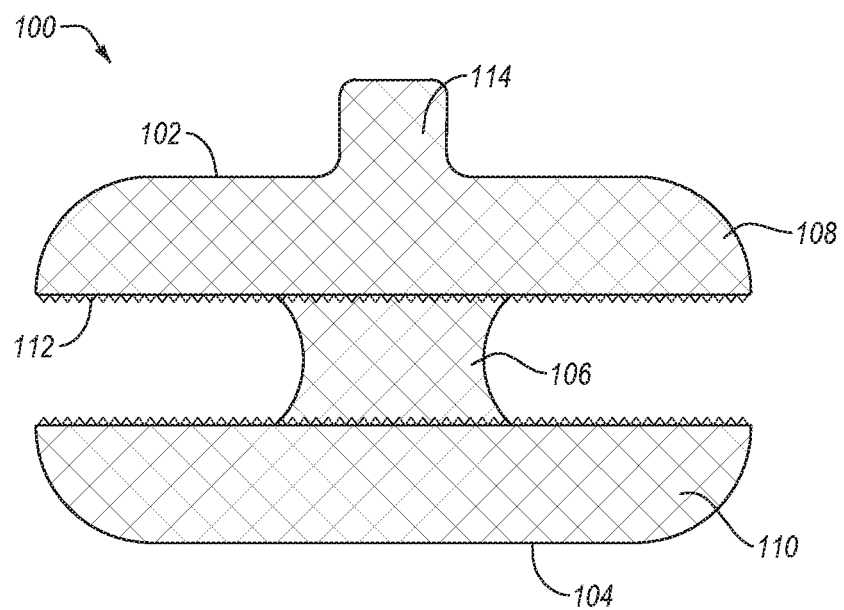
FIG. 5 illustrates an exemplary embodiment of a repair device that may be utilized to perform a tricuspid repair procedure as described herein.

FIG. 5 'illustrates an embodiment of a repair device 100 that may be utilized to reduce or eliminate regurgitation in a defective valve, such as a regurgitant tricuspid valve. The illustrated embodiment has a proximal end 102 and a distal end 104. As shown, a proximal disk 108 is disposed opposite a distal disk 110, with the proximal disk 108 disposed toward the proximal end 102 and the distal disk 110 disposed toward the distal end 104. The proximal disk 108 and the distal disk 110 are joined by a neck section 106. As shown, the neck section 106 has a smaller diameter than the adjoining disks 108 and 110. In some embodiments, a ratio of a diameter of the neck section 106 to a diameter of one or both of the disks 108 and 110 is about 0.05, 0.1, 0.2, 0.3, 0.4, 0.5, or 0.6, or is within a range having endpoints defined by any two of the foregoing values.

Although the exemplary embodiment illustrated here includes disk-shaped members 108 and 110, it will be understood that similar components and principles described herein may be applied to embodiments having members of other shapes. For example, some embodiments may include elements having a polygonal profile, as opposed to a rounded disk profile. In some embodiments, a polygonal profile can aid in the flexure performance and/or the folding and unfolding functionality of the repair device.

The proximal disk 108 and distal disk 110 are positioned relative to one another to define a grasping space therebetween. When deployed, the repair device 100 is positioned so as to grasp valve leaflets between the proximal disk 108 and the distal disk 110. In some embodiments, the repair device 100 is configured such that the size and shape of the grasping space between the disks 108 and 110 matches targeted tricuspid valve anatomy. For example, a distance between the proximal disk 108 and the distal disk 110 may be sized as approximately the same thickness of targeted tricuspid valve leaflets or slightly smaller than the thickness of the leaflets so as to provide sufficient engagement of the repair device 100 with the leaflets.

In the illustrated embodiment, the neck section 106 is positioned to join the opposing disks 108 and 110 at the center of each opposing disk 108 and 110. In other embodiments, a neck section is offset from the center of one or both opposing disks. In the illustrated embodiment, the proximal disk 108 and the distal disk 110 are substantially the same in size and shape. In other embodiments, a disk may have a differently configured size and/or shape than the opposite disk. For example, repair device having an offset neck section and/or having differently sized disks may be utilized in applications where a targeted valve has unique anatomy, in circumstances where particular regions of a targeted valve require greater coverage and/or grasping surface area, and/or in other implementations where a non-symmetrical configuration can provide interventional benefits.

The illustrated embodiment also includes a plurality of grip elements 112 extending from the opposing disks 108 and 110. The grip elements 112 may be configured as tines, barbs, ridges, or other structures for enhancing engagement of the repair device 100 with targeted tissue grasped between the opposing disks 108 and 110 when the repair device is deployed. In the illustrated embodiment, each of the opposing disks 108 and 110 include grip elements 112 positioned so as to face and/or extend toward the opposite disk in the grasping space. In other embodiments, grip elements may be omitted, or may be included on some sections of the device and omitted on others (e.g., included on one disk but not the opposite disk and/or included at only portions of a disk).

The illustrated embodiment also includes a connection element 114 configured to enable connection of the repair device 100 to one or more separate interventional tools, such as a delivery catheter or delivery rod, as explained in more detail below. In some embodiments, the repair device 100 includes a wireframe structure enabling the repair device 100 to be moved between a collapsed configuration and an expanded/deployed configuration. In some embodiments, the repair device 100 is formed from a superelastic/shape-memory material, such as nitinol, enabling the device to be compressed into the collapsed configuration (e.g., for transcatheter delivery) without plastic deformation so that it may return to the expanded configuration upon deployment.

In the illustrated embodiment, the opposing disks 108 and 110 are configured so that the opposing gripping surfaces are substantially parallel with one another. In other embodiments, one or both disks may be shaped so as to provide a gripping surface with a tapering and/or non-linear profile. For example, along a path from a radially central location of a gripping surface (e.g., near the neck section) moving toward the periphery, the corresponding disk may be shaped such that the gripping surface tapers further toward or further away from the opposing gripping surface. Such a configuration may be utilized to better match the shape of targeted valve tissue (e.g., leaflets), to provide better engagement once deployed, and/or to conform to unique anatomy of a particular patient, for example.

Figure 6:
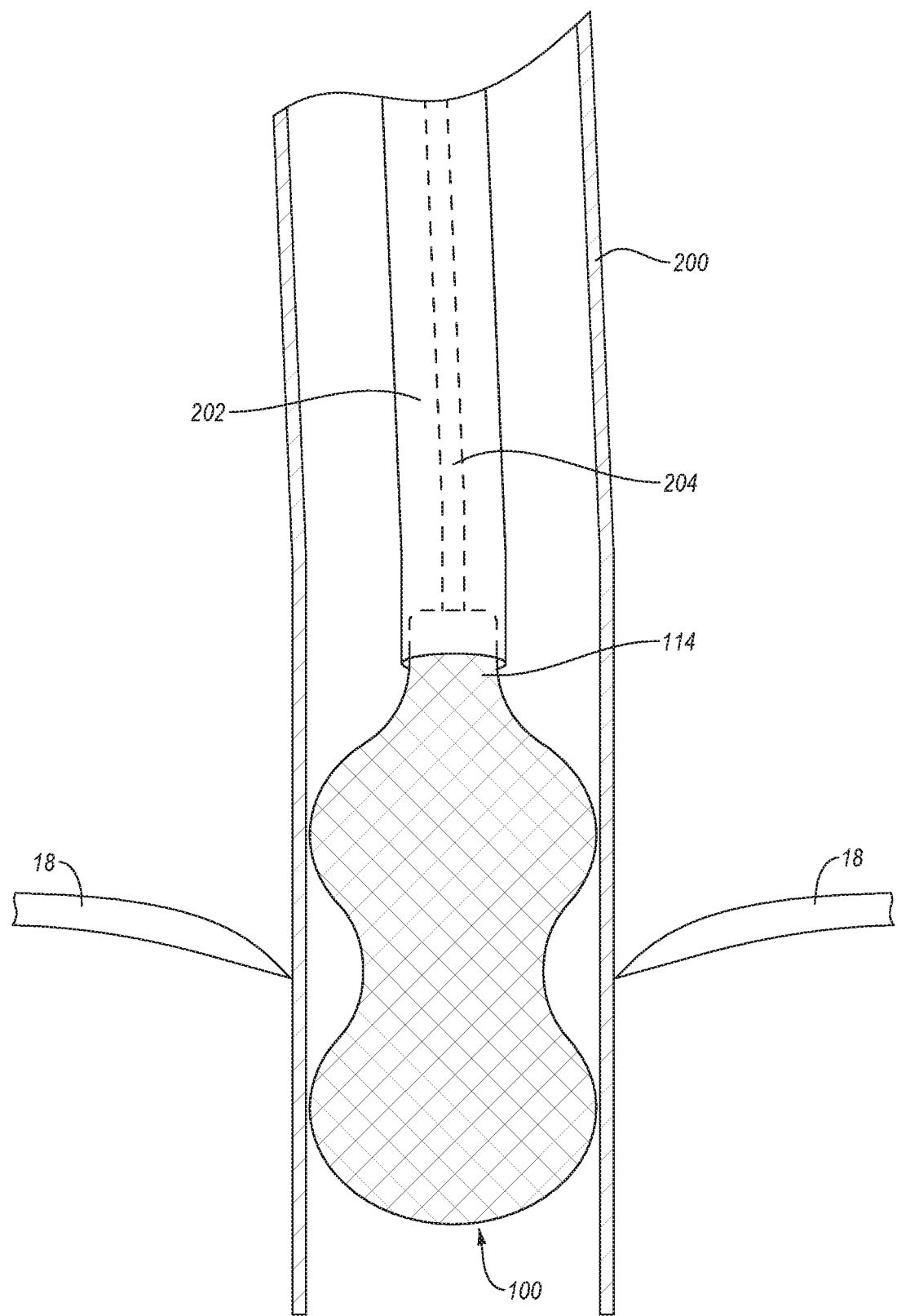
FIGS. 6-9 illustrate delivery and deployment of the repair device in a tricuspid repair procedure, showing deployment of the repair device through a delivery system so as to grasp leaflet tissue in a deployed position.

FIGS. 6-9 illustrate a system and method of delivering and deploying the repair device 100 at a targeted tricuspid valve 18 to repair the tricuspid valve 18 and reduce or eliminate regurgitation through the valve 18. FIG. 6 illustrates the repair device 100 in a collapsed configuration within a delivery system. The delivery system includes a delivery catheter 202 positioned within a sheath 200. As shown, the connection element 114 of the repair device 100 is coupled to a connection element 204 of the delivery catheter 202 at a distal portion of the delivery catheter 202. The connection elements 204 and 114 are detachably engaged with one another through a mechanical linkage (e.g., one or more clips, pins, threaded engagements, tabs, slots, or other fastener components), magnetic linkage, and/or other fastening means.

In the illustrated embodiment, the delivery catheter 202 is translatable relative to the sheath 200 so that the repair device 100 may be positioned relative to the sheath 200 through translation of the delivery catheter 202.

As depicted in FIG. 6, the distal end of the delivery system is passed from a position in the right atrium, superior to the tricuspid valve 18, past the tricuspid valve so as to extend into the right ventricle. For example, the delivery system may be routed to the tricuspid valve 18 through a transjugular approach through the superior vena cava and into the right atrium. Alternatively, the delivery system may be routed to the targeted valve through a transfemoral approach, transapical approach, or other approach. As shown, the delivery system is positioned so that the distal end of the repair device 100 extends past the tricuspid valve 18 and into the right ventricle, while the proximal end of the repair device 100 remains on the atrial side of the valve 18.

Figure 7:
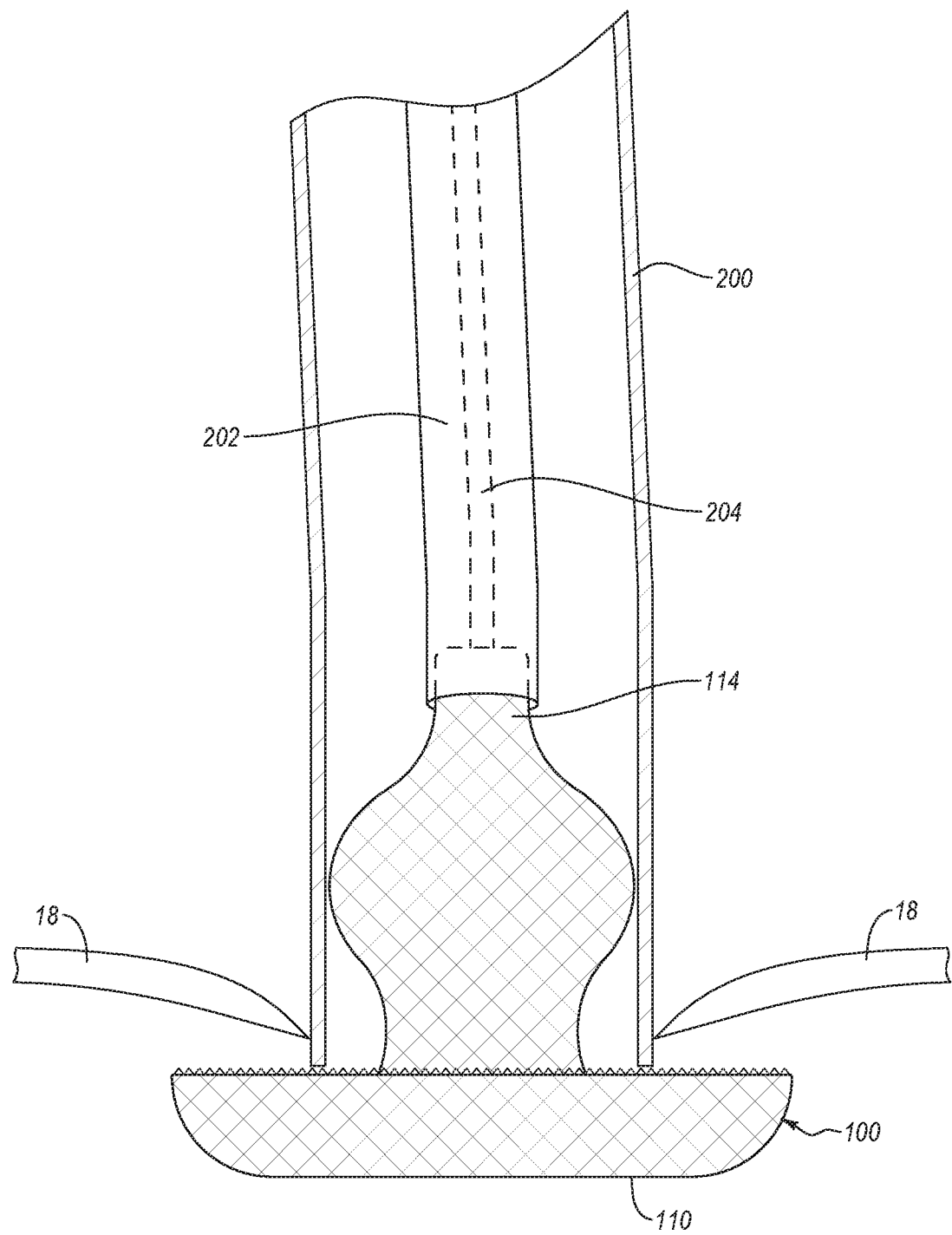

From this position, the sheath 200 may be partially retracted so as to allow the distal section of the repair device 100 to expand to deploy the distal disk 110 on the ventricular side of the valve 18, as shown in FIG. 7. Although the illustrated embodiment shows deployment as a result of proximal retraction of the sheath 200 relative to the delivery catheter 202 and the repair device 100, alternative implementations may deploy the repair device 100 by distally pushing the delivery catheter 202 relative to the sheath 200 or through a combination of distally pushing the delivery catheter 202 and proximally retracting the sheath 200.

Figure 8:
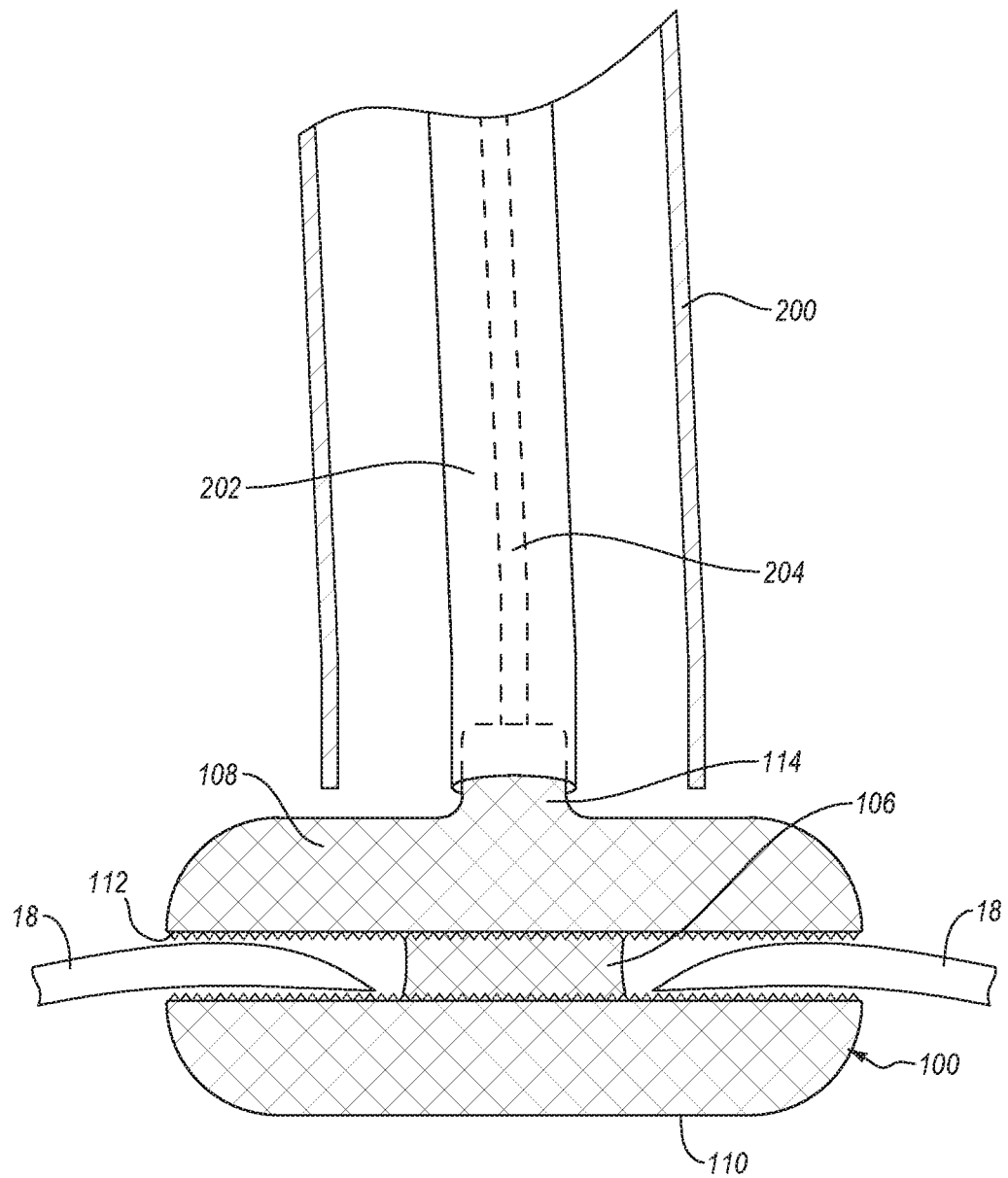

As shown in FIG. 8, continued retraction of the sheath 200 relative to the delivery catheter 202 and the repair device 100 allows the proximal section of the repair device 100 to expand so as to deploy the proximal disk 108 on the atrial side of the valve 18. As the proximal disk 108 deploys, the leaflets of the tricuspid valve 18 are fixed between the opposing disks 108 and 110, enabling the repair device 100 to maintain the captured leaflets in a position that reduces or eliminates regurgitation through the valve 18.

In some implementations, the repair device 100 may be selectively retracted by re-sheathing the proximal disk 108. For example, to adjust the positioning of the repair device 100 relative to the leaflets of the valve 18 and/or to attempt a better grasping of leaflets, the proximal disk 108 may be pulled back into the sheath 200 (and/or the sheath 200 may be pushed over the proximal disk 108), placing the device back into the configuration shown in FIG. 7. The device may then be readjusted or repositioned before re-deploying the proximal sheath 108 to grasp the leaflets again. In some circumstances, the repair device 100 may be fully retracted back to the configuration shown in FIG. 6. For example, the repair device 100 may be fully retracted if a procedure is aborted or if further monitoring or analysis is required.

Figure 9:
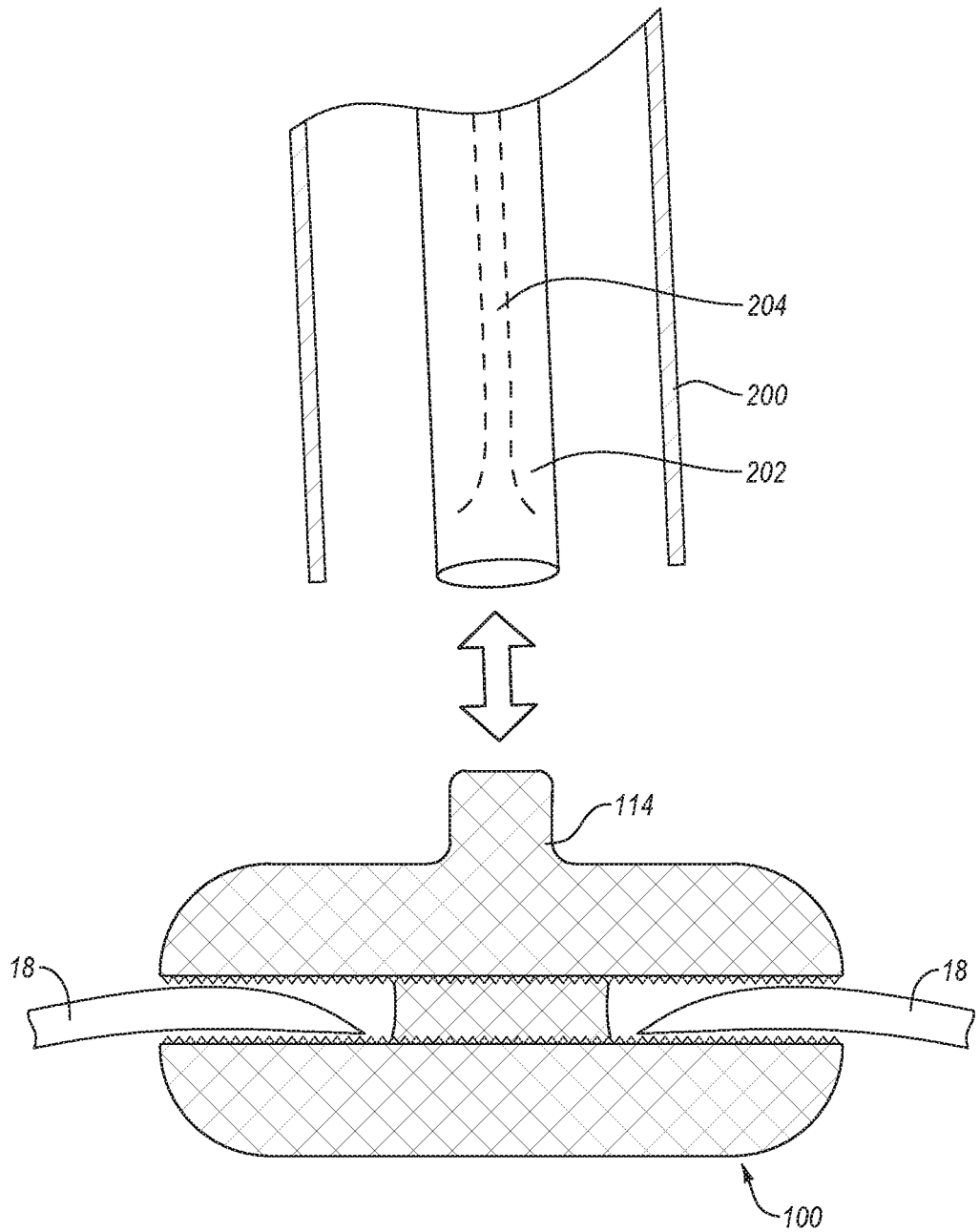

As shown in FIG. 9, after the repair device 100 has been deployed to grasp the leaflets of the valve 18, the delivery catheter 202 may be decoupled from the connection element 114, and the sheath 200 and delivery catheter 202 may be removed from the treatment site. The repair device 100 remains in position with the leaflets fixed to minimize or eliminate regurgitation through the valve 18. As shown, the corresponding connecting elements 114 and 204 are decoupled from one another to enable detaching of the repair device 100 from the remainder of the delivery system. The connecting elements 114 and 204 may be decoupled by actuating a mechanical linkage to disconnect the respective elements (e.g., unclasping, unscrewing, removing tabs from slots, and/or other means of detaching a mechanical fastening), uncoupling a magnetic connection, or otherwise disengaging the connection elements 114 and 204.

Although the example depicted in FIGS. 6-9 illustrate an approach in which the repair device 100 is routed to the valve 18 from a position superior prior to deployment (e.g., through a transjugular approach), it will be understood that the described principles and features may be applied to other approaches as well. For example, in a transapical approach, the repair device 100 may be inserted into the right ventricle and then be passed from a position inferior to the tricuspid valve through the valve and into a position superior to the valve. In the illustrated implementation, the repair device 100 is deployed by first deploying the distal disk 110 on the inferior (ventricular) side of the valve 18, and then further deploying the proximal disk on the superior (atrial) side of the valve 18. It will be understood that from an inferior approach, the repair device 100 may be deployed by first deploying the distal disk 110 on the superior (atrial) side of the valve, and then deploying the proximal disk on the inferior (ventricular) side of the valve.

Figure 10:
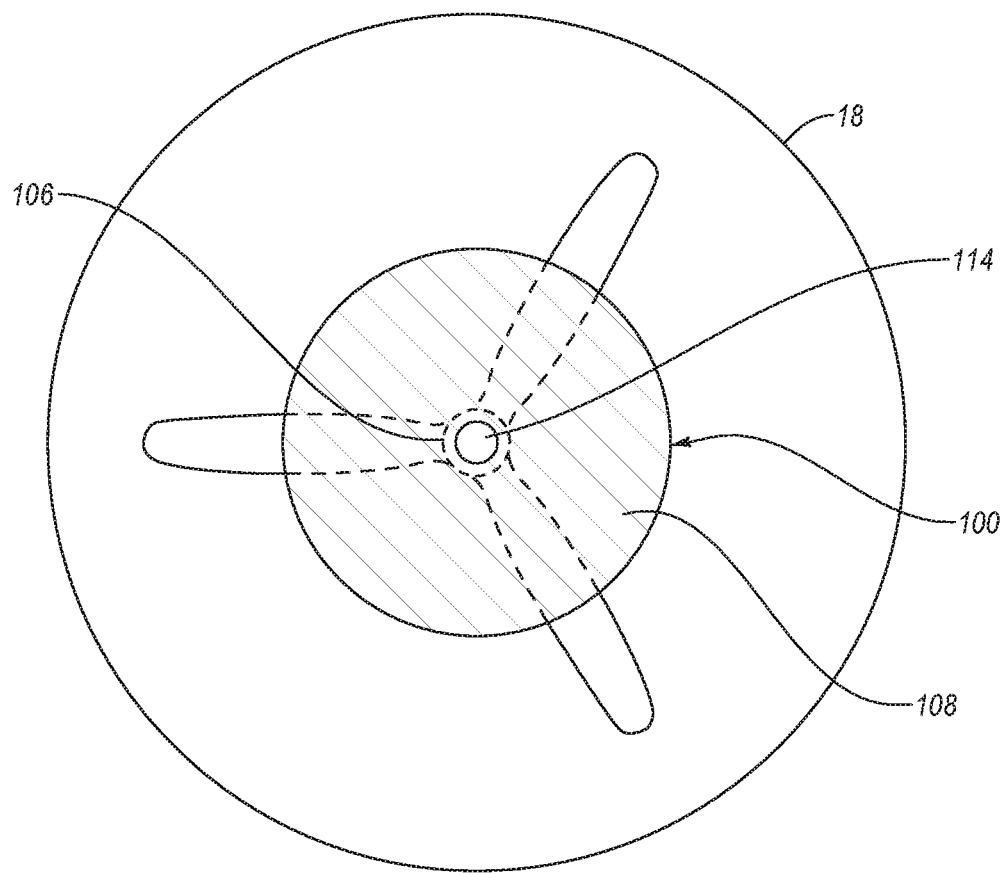
FIG. 10 illustrates a superior view of a tricuspid valve showing the repair device in a deployed position.

FIG. 10 illustrates a superior view of the tricuspid valve 18 showing the repair device 100 in a deployed state and showing the proximal disk 108 oriented on the atrial side of the valve 18. As shown, the opposing disks of the repair device 100 beneficially grasp and fix the three leaflets of the tricuspid valve 18. At least some of the embodiments described herein are able to provide simultaneous grasping of all three of the tricuspid leaflets, offering the advantage of a straightforward deployment process uncomplicated by the need to make multiple grasping maneuvers to properly engage with all three of the tricuspid valve leaflets.

For example, during a valve repair procedure, it can often be difficult to properly position a repair device relative to the targeted site and/or to grasp targeted leaflets because the position of the leaflets and other tissues are in dynamic flux. In particular, the challenge is compounded for repair procedures related to the tricuspid valve, where there are three separate leaflets within the treatment environment. One or more of the embodiments described herein enable simultaneous grasping of all three leaflets, enhancing the likelihood of successful deployment, lowering the number of readjustment maneuvers, and reducing procedure time, for example.

Further, less positional accuracy of the device prior to deployment is required as a result of the relatively wide profile of the opposing disks. The opposing disks function to broaden the acceptable range of deployment positions capable of successfully grasping all three leaflets in a manner that sufficiently treats the regurgitant condition. As described, positioning and orienting a delivery system prior to deployment can be challenging due to the dynamic nature of the treatment environment. A more forgiving positioning requirement allows for faster procedures and less need for multiple grasping attempts, for example.

Figure 11:
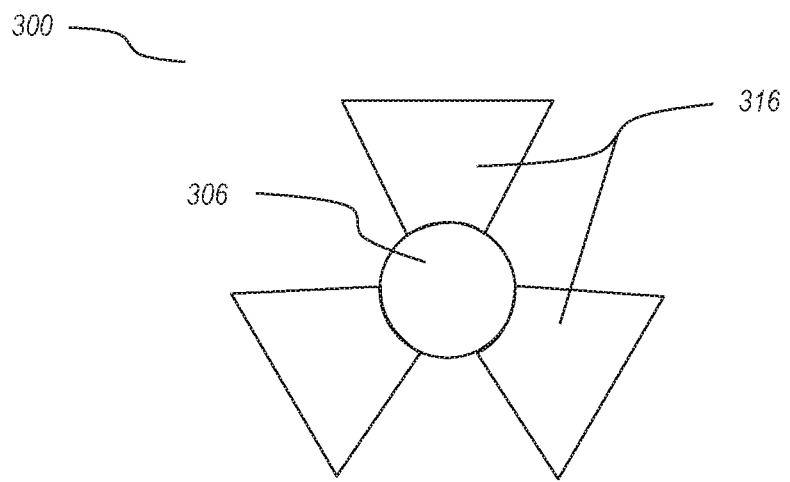
FIGS. 11 and 12 illustrate another embodiment of a repair device including grasping elements attached to a central shaft with a hinged attachment.
Figure 12:
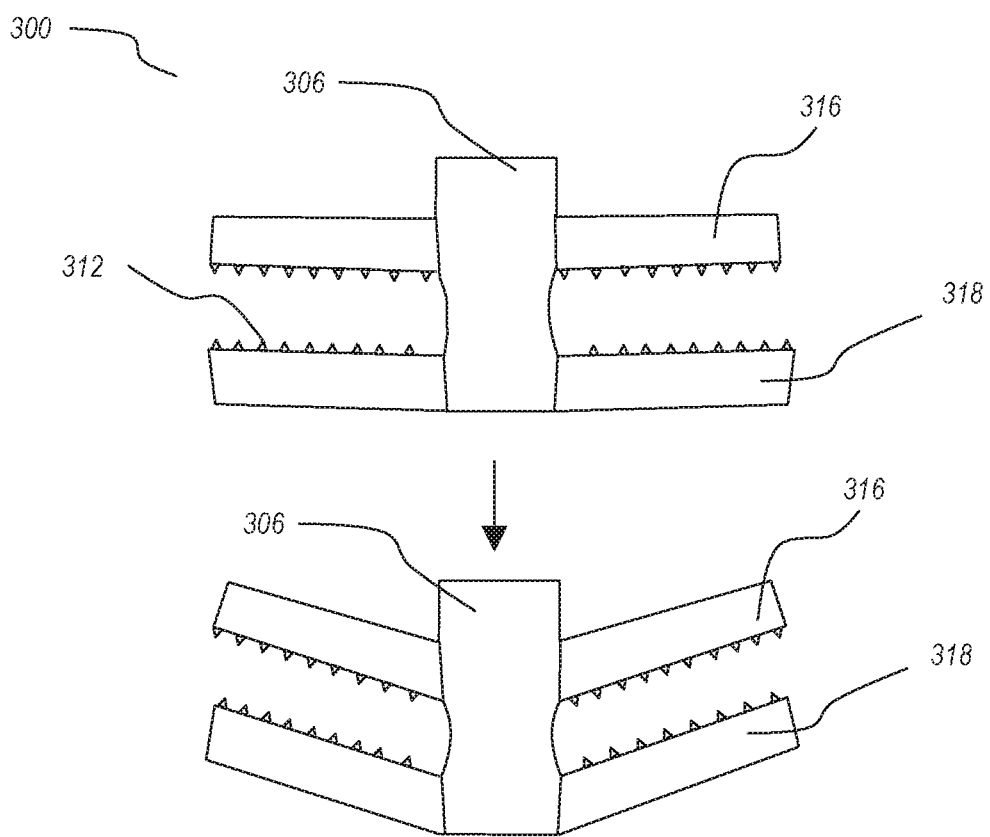

FIGS. 11 and 12 illustrate another embodiment of a repair device 300 which can be utilized in a cardiac valve repair procedure, such as a regurgitant tricuspid valve repair procedure. FIG. 11 illustrates a top/plan view of the device 300 and FIG. 12 illustrates a front view of the device 300. As shown by FIG. 12, the repair device 300, when deployed, includes a profile configured to aid in flexing between a collapsed configuration and an expanded configuration. In the illustrated embodiment, the disks/disk-like members of the device 300 include three separate proximal grasping elements 316 and three separate distal grasping elements 318. Other embodiments may include one or both sides (proximal and/or distal) having two grasping elements, or more than three grasping elements.

In the illustrated embodiment, the grasping elements 316 and 318 are substantially aligned so that each corresponding pair is capable of grasping leaflet tissue between the pair. In alternative embodiments, one or more of the proximal grasping elements 316 may be offset from the distal grasping elements 318, or vice versa. Some embodiments may omit grasping elements at certain sections of the device. For example, some embodiments may include a distal section formed as a disk (such as distal section 110 of repair device 100 described above), and include a proximal section having grasping elements 316. Likewise, some embodiments may include a distal section having grasping elements 318, and include a proximal section formed as a disk (such as proximal section 108 of repair device 100 described above).

The grasping elements 316 and 318 may be symmetrically arranged about a central shaft 306 (which includes a neck section between the grasping elements), as shown. Alternatively, one or more grasping elements 316, 318 may be offset to form an asymmetric arrangement. The grasping elements 316, 318 may be sized for different anatomical and/or procedural needs. For example, different grasping elements 316, 318 may be sized according to the tricuspid valve leaflets of a particular patient in order to provide a desired level of leaflet constraint when deployed.

In some embodiments, the repair device 300 is formed as a wireframe structure, such as a wireframe structure of nitinol. Alternatively, one or more sections, such as the grasping elements 316 and/or 318, may be formed as separate structures, such as solid sections of polymer, stainless steel, nitinol, cobalt-chromium alloy, other suitable materials, or combinations thereof. As shown, the grasping elements 316, 318 may include one or more grip elements 312, which may be configured similar to the grip elements 112 of the repair device 112 illustrated in FIG. 5.

In the illustrated embodiment, the grasping elements 316 and 318 are formed as fan-shaped elements that continuously broaden as they extend from the central shaft 306 to their perimeters. Alternative embodiments may include one or more grasping elements having different shapes, such as extensions that do not broaden or that broaden in a discontinuous fashion, such as only at a perimeter section. As shown, the grasping elements 316 and 318 are configured so as to make up about half of the plan view surface area of the device. For example, as best shown by the plan view of FIG. 11, the grasping elements 316 make up about as much of the plan view surface area as do the spaces in between each of the grasping elements 316 (e.g., considering the plan view surface area to be defined by a circle circumscribing the plan view of the device). In other embodiments, the grasping elements may be configured to make up about 20%, 40%, 60%, or 80% of the plan view surface area of the device, or to make up an amount of plan view surface area within a range defined by any two of the foregoing values.

In the illustrated embodiment, the grasping sections 316 and 318 are connected to the central shaft 306. Beneficially, the central shaft 306 functions as a hinge point for the separate grasping sections 316 and 318, enabling the grasping sections to flex according to the movement of grasped valve leaflets after the repair device 300 has been deployed within a cardiac valve. In some implementations, the separate grasping sections 316, 318 are able to independently flex at the respective hinge points of the central axis 306 so as to independently provide the needed flexure at each particular grasping section 316 (e.g., to provide different flexure for each of the separate tricuspid valve leaflets).

FIG. 12 shows the repair device 300 showing the grasping elements 316 and 318 moving from a neutral position into an exemplary flexed position. For example, tricuspid valve leaflets will move somewhat downward (i.e., towards the right ventricle) to open the valve during diastole, and will then move upward (i.e., toward the right atrium) to coapt with one another and close the valve during systole. The flex provided by the repair device 300 allows the leaflets to move and/or coapt with one another without being overly constrained.

In some embodiments, the central shaft 306 and the grasping elements 316, 318 are integrally joined, and the central shaft 306 functions as a hinge as a result of the inherent flexibility and resiliency of the joint formed by the central shaft 306 and the grasping elements 316, 318. In other embodiments, one or more grasping elements are coupled to the central shaft 306 by a mechanical hinge that enables proximal and/or distal rotation of the corresponding grasping element.

Delivery and deployment of the repair device 300 may be carried out in a manner similar to the process illustrated in FIGS. 6 to 9, by retracting a sheath and/or pushing a delivery catheter so as to allow the device to expand into a deployed state. Accordingly, the delivery system illustrated in FIGS. 6 to 9 may be utilized to deliver the repair device 300, or any other interventional repair devices described herein. In some embodiments, the central shaft 306 may include and/or may function as a connection element for coupling with a delivery catheter such as in FIGS. 6 to 9.

Figure 13:
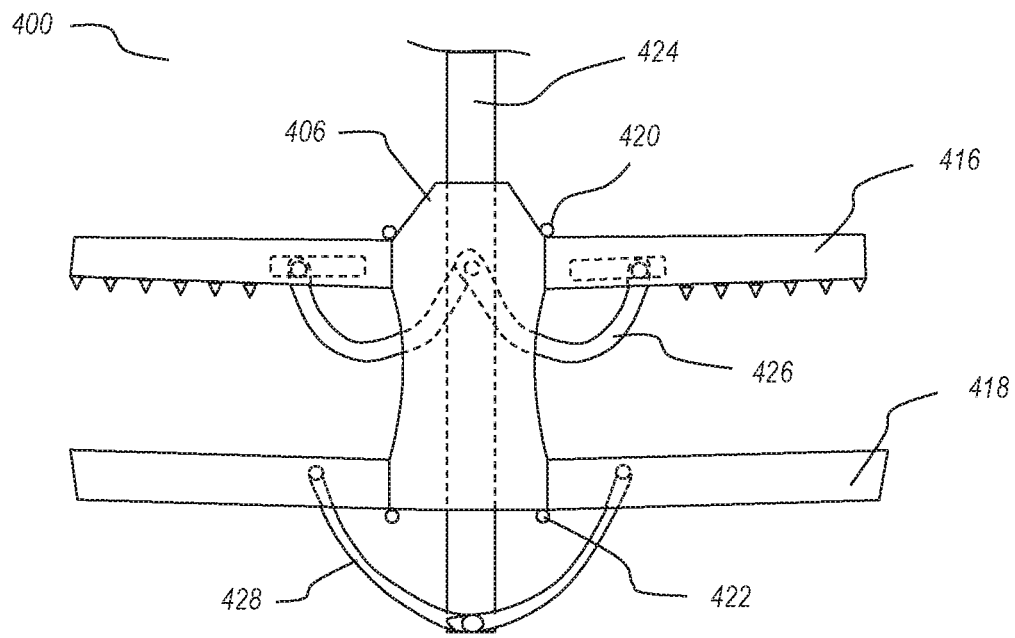
FIGS. 13 and 14 illustrate an embodiment of a repair device having an actuation mechanism controllable by translation of an actuation rod.

FIG. 13 illustrates an embodiment of a repair device 400 having an actuation mechanism for controlling the actuation of grasping elements 416 and 418 about hinge points 420 and 422. The actuation mechanism described herein may be utilized to actuate any of the grasping elements described herein, such as any of the grasping elements 316, 318 described in relation to FIGS. 11 and 12. The repair device 400 may be delivered using one or more delivery system components illustrated in FIGS. 6 to 9. For example, the central shaft 406 may include and/or may function as a connection element to provide attachment to the delivery catheter 202.

FIG. 13 illustrates the repair device 400 with the grasping elements 416 and 418 in a deployed position, such as they would appear when grasping cardiac valve tissue. As shown, an actuator rod 424 extends through the central shaft 406. Proximal legs 426 are pivotably coupled to the actuator rod 424 and are respectively joined to each proximal grasping element 416. Likewise, distal legs 428 are pivotably coupled to the actuator rod 424 and are respectively joined to each distal grasping element 418.

Figure 14:
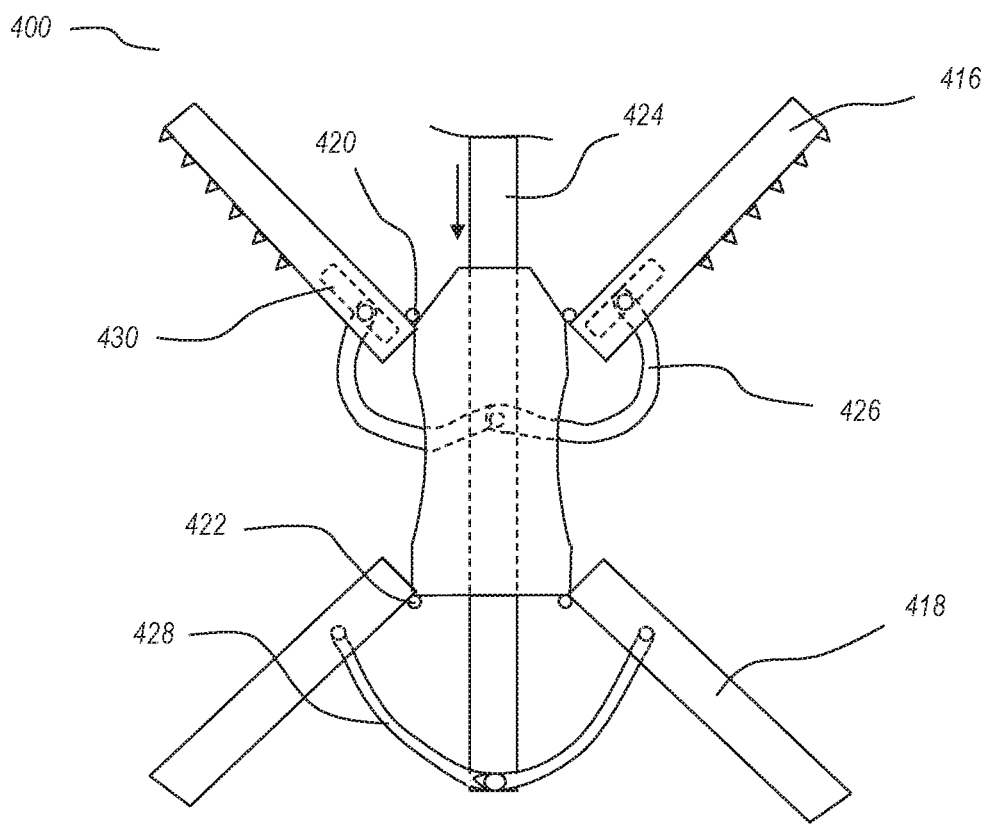

FIG. 14 illustrates actuation of the actuation rod 424 to move the repair device into a collapsed configuration, such as one having a smaller profile suitable for delivery to the targeted treatment site, or such as one that allows repositioning of the device and/or regrasping of targeted tissue. As indicated, distal translation of the actuator rod 424 relative to the central shaft 406 pushes the distal legs 428 further distally. The distal legs 428 thereby act to pull on the distal grasping elements 418, causing them to rotate about hinge points 422 to rotate away from central shaft 406 into a position relatively more parallel with the central shaft 406.

In this embodiment, the mechanism associated with the proximal grasping elements 416 works in a slightly different manner. As shown, distal translation of the actuator rod 424 causes the proximal legs 426 to move distally. Because of the curvature of the proximal legs 426 (shown in this embodiment as having a proximally-facing concavity or "C" shape), the distal movement of the legs 426 at the point where they connect to the actuator rod 424 causes the opposite ends, which are joined to respective proximal grasping elements 416, to rotate inwardly toward the actuator rod 424. This inward rotation pushes proximally against the proximal grasping elements, causing them to rotate about hinge points 420 to move to a position more parallel to the central shaft 406. In the illustrated embodiment, the proximal grasping elements 416 also include slots 430 to enable inward movement of the proximal legs 426 as they rotate inwardly and push proximally against the proximal grasping elements 416.

The illustrated actuation mechanisms beneficially enable an operator to selectively move the grasping elements 416, 418 between an open position, where the device is free to be repositioned relative to targeted anatomy, and a deployed position, where grasping of the tissue may be maintained. In contrast to a repair device that relies solely on self-expanding components, which may only provide one attempt at proper positioning and deployment, the illustrated repair device 400 enables repeated attempts at deployment and thereby increases the likelihood of a successful procedure.

Figure 15:
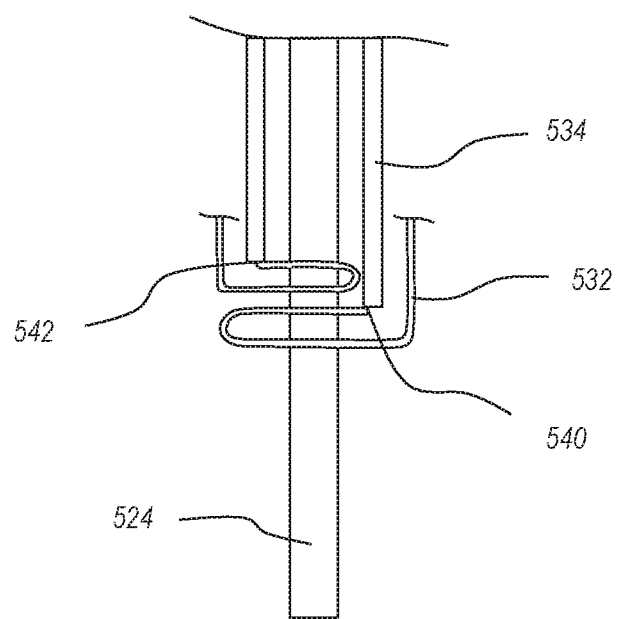
FIGS. 15 and 16 illustrate an embodiment of a locking mechanism that may be utilized during deployment of a repair device, enabling release and repositioning of the repair device.
Figure 16:
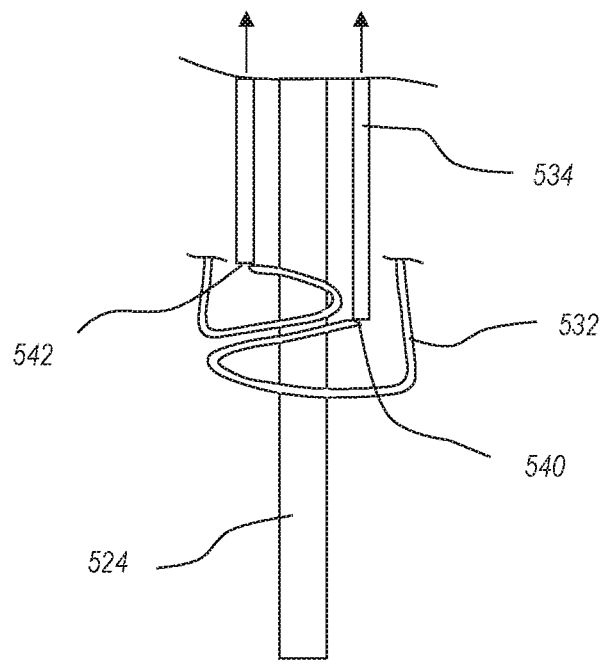

FIGS. 15 and 16 illustrate an embodiment of a locking mechanism that may be utilized with a repair device described herein, such as the repair device 400 of FIGS. 13 and 14 (in this illustration, other repair device components such as a central shaft, grasping elements, and actuation mechanisms, have been removed for clarity). FIG. 15 shows an actuator rod 524 passed through a series of locking plates 532. The locking plates 532 include holes allowing passage of the actuator rod 524. In FIG. 15, the locking plates 532 are shown in an open configuration where plates are positioned so that the holes of the plates are sufficiently aligned to allow translation of the actuator rod 524. In FIG. 16, the locking plates 532 are shown in a binding configuration, where the plates are moved to a position where the holes are out of alignment and the locking plates 532 therefore bind against the actuator rod 524.

The illustrated embodiment also includes a lock control 534. In the illustrated embodiment, the locking plates 532 are biased toward the binding configuration of FIG. 16. When the lock control 534 is moved proximally from the open configuration of FIG. 15, it no longer presses against the locking plates at abutment points 540 and 542, allowing the plates to move toward the binding configuration of FIG. 16. To unlock the actuator rod 524, the lock control 534 may be moved distally to re-engage with the abutment points 540 and 542, bending the locking plates 532 to the open position of FIG. 15. The lock control 534 may be joined to the abutment points 540 and 542, or may be sized so as to contact them when translated sufficiently distally.

The lock control 534 may extend proximally through a delivery catheter (such as the delivery catheter shown in FIGS. 6 to 9), or may be coupled to a control line that extends proximally through the catheter, and may be actuated using a handle or other control mechanism coupled to a proximal end of the delivery catheter. The free ends of the locking plates 532 (the ends opposite the abutment points 540 and 542) may be coupled to an interior surface of the central shaft through which the actuator rod 524 passes through and is translatable through. Alternatively, the free ends may be attached to the proximal grasping elements, or to some other structure separate from the actuator rod 524.

Alternative embodiments may include one or more locking plates that are biased toward an open configuration rather than a binding configuration. For example, some embodiments may include locking plates biased toward the configuration shown in FIG. 15, and locking the actuator rod 524 requires pulling the lock control 534 so as to pull the locking plates at abutment points 540 and 542 to move to the binding configuration of FIG. 16.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Figure 17:
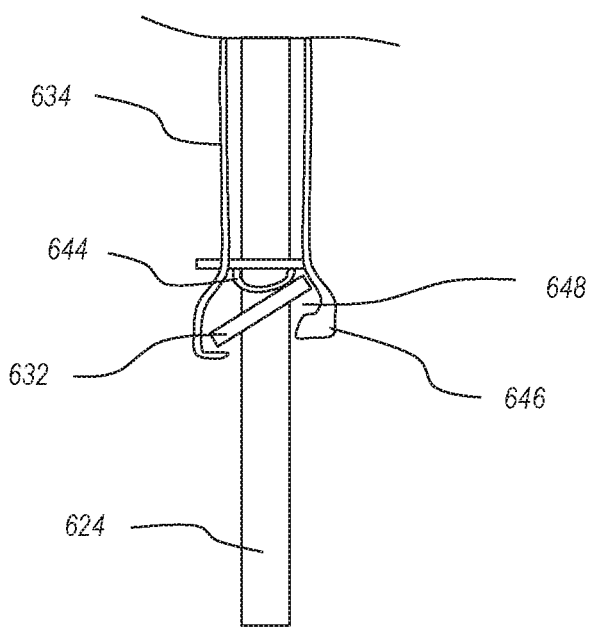
FIGS. 17 and 18 illustrate another embodiment of a locking mechanism that may be utilized during deployment of a repair device, enabling release and repositioning of the repair device.
Figure 18:
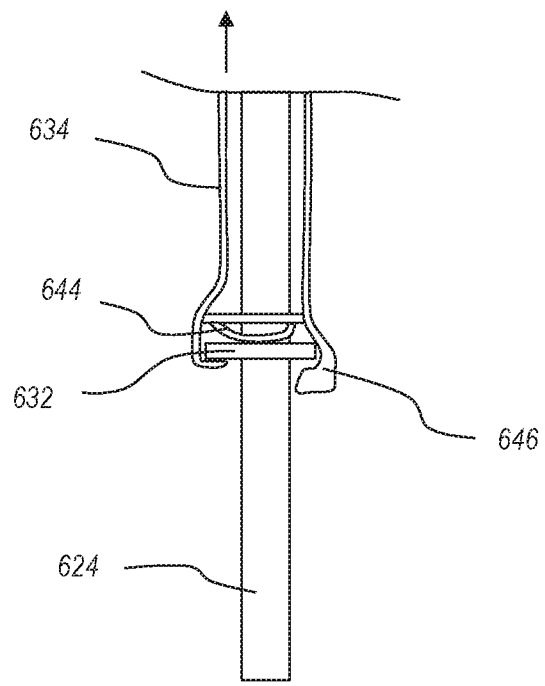

FIGS. 17 and 18 illustrate another embodiment of a locking mechanism that may be utilized with any of the repair devices described herein (in the illustrated embodiment, other repair device components such as a central shaft, grasping elements, actuation mechanism, etc. have been removed for clarity). FIG. 17 illustrates an actuator rod 624 passed through a locking plate 632. The locking plate 632 includes a hole allowing passage of the actuator rod 624. In FIG. 17, the locking plate 632 is forced, by default, into an angled position by a leaf spring 644. In the angled position, the hole of the locking plate 632 is also angled with respect to the actuator rod 624, causing the locking plate 632 to bind against the actuator rod 624, effectively locking and preventing translation of the actuator rod. In some embodiments, the actuator rod 624 includes grooves or channels corresponding to locked positions, the grooves or channels functioning to enhance the engagement and binding of the edge of the hole of the locking plate 632 when it is in the angled position.

FIG. 18 shows the actuator rod 624 in the unlocked position. As shown, a lock control 634 may be moved proximally relative to the leaf spring 644 and the actuator rod 624, thereby engaging with and pulling the locking plate 632 into a position more perpendicular to the longitudinal axis of the actuator rod 624. In this position, the locking plate hole through which the actuator rod 624 passes does not bind against the actuator rod 624, allowing the actuator rod 624 to freely translate. The lock control 634 may extend proximally through a delivery catheter (such as the delivery catheter shown in FIGS. 6 to 9), or may be coupled to a control line that extends proximally through the catheter, and may be actuated using a handle or other control mechanism coupled to a proximal end of the delivery catheter.

In the illustrated embodiment, a holding structure 646 is disposed opposite the lock control 634, and is configured to maintain the locking plate 632 in position against the leaf spring 644. As shown, the holding structure 646 is shaped to define a pivot space 648 to allow one end of the locking plate 632 to pivot when the locking plate 632 is moved from the angled position to the more perpendicular position.

Elements described in relation to any embodiment depicted and/or described herein may be combinable with elements described in relation to any other embodiment depicted and/or described herein. For example, any element described in relation to a repair device of FIGS. 5 to 10 may be combinable with any element described in relation to a repair device of FIGS. 11 and 12, an actuation mechanism of FIGS. 13 and 14, and/or a locking mechanism of FIGS. 15 and 16.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for repairing a targeted cardiac valve, the method comprising:
   positioning a repair device at a targeted cardiac valve, the repair device being moveable between a collapsed configuration and an expanded configuration, the repair device comprising:
      a proximal grasping assembly movable between a first position and a second position;
      a distal grasping assembly movable between a third position and a fourth position, the distal grasping assembly being spaced apart from the proximal grasping assembly so as to define a grasping space therebetween for grasping tricuspid valve leaflets when the proximal grasping assembly and the distal grasping assembly are in second position and fourth position, respectively, and are deployed at a tricuspid valve; and
      an actuator rod mounted operatively connected to each of the proximal grasping assembly and the distal grasping assembly so that distal movement of the actuator rod simultaneously moves the proximal grasping assembly proximally and the distal grasping assembly distally;
   deploying the distal grasping assembly and the proximal grasping assembly to capture targeted cardiac valve tissue between the distal grasping assembly and the proximal grasping assembly.

2. The method of claim 1, wherein the targeted cardiac valve is a tricuspid valve, and wherein the targeted cardiac valve tissue includes the leaflets of the tricuspid valve.

3. The method of claim 2, wherein deployment of the proximal grasping assembly and the distal grasping assembly simultaneously captures the three leaflets of the tricuspid valve.

4. The method of claim 2, wherein the grasping space is sized and shaped to conform to an anatomical shape of the targeted tricuspid valve leaflets.

5. The method of claim 2, wherein the distal grasping assembly is deployed on a ventricular side of the targeted tricuspid valve, and wherein the proximal grasping assembly is deployed on an atrial side of the targeted tricuspid valve.

6. The method of claim 1, wherein the actuator rod is slidably received within a central shaft to which are pivotally mounted the proximal grasping assembly and the distal grasping assembly.

7. The method of claim 6, further comprising a first proximal leg connecting a first proximal arm of the proximal grasping assembly to the central shaft and a second proximal leg connecting a second proximal arm of the proximal grasping assembly to the central shaft.

8. The method of claim 7, wherein each of first proximal leg and the second proximal leg is formed with a proximally facing concavity.

9. The method of claim 1, further wherein deploying the distal grasping assembly and the proximal grasping assembly comprises distally advancing the actuator rod to simultaneously move the proximal grasping assembly proximally and the distal grasping assembly distally.

10. The method of claim 9, wherein the proximal grasping assembly rotates proximally, and the distal grasping assembly rotates distally with respect to the central shaft with distal movement of the actuator rod.

11. The method of claim 10, further comprises moving a first distal leg connecting the central shaft and the first distal arm inwardly and moving a first proximal leg connecting the central shaft and the first proximal arm outwardly with distal advancing of the actuator.

12. An interventional device configured for repair of a regurgitant tricuspid valve, the repair device comprising:
   a proximal grasping assembly movable between a first position and a second position;
   a distal grasping assembly movable between a third position and a fourth position, the distal grasping assembly being spaced apart from the proximal grasping assembly so as to define a grasping space therebetween for grasping tricuspid valve leaflets when the proximal grasping assembly and the distal grasping assembly are in second position and fourth position, respectively, and are deployed at a tricuspid valve; and
   an actuator rod mounted operatively connected to each of the proximal grasping assembly and the distal grasping assembly so that distal movement of the actuator rod simultaneously moves the proximal grasping assembly proximally and the distal grasping assembly distally.

13. The interventional device of claim 12, wherein the distal grasping assembly comprises a first distal arm and a second distal arm, each being pivotally mounted to a central shaft receiving the actuator rod.

14. The interventional device of claim 13, further comprising a first distal leg mounted to the first distal arm and the central shaft and a second distal leg mounted to the second distal arm and the central shaft, the first distal leg and the second distal leg are curved to move the first distal arm and the second distal arm distally with distal movement of the actuator rod.

15. The interventional device of claim 12, wherein the proximal grasping assembly comprises a first proximal arm and a second proximal arm, each being pivotally mounted to a central shaft receiving the actuator rod.

16. The interventional device of claim 15, further comprising a first proximal leg mounted to the first proximal arm and the central shaft and a second proximal leg mounted to the second proximal arm and the central shaft, the first proximal leg and the second proximal leg are curved to move the first proximal arm and the second proximal arm proximal with distal movement of the actuator rod.

17. The interventional device of claim 16, wherein the first proximal leg and the second proximal leg have a proximally facing concavity.

18. An interventional system configured for repair of a regurgitant tricuspid valve, the repair system comprising:
   a delivery system, comprising:
      a sheath;
      a delivery catheter disposed within the sheath so as to be translatable within the sheath, the delivery catheter including a connection element disposed at a distal end of the delivery catheter; and
   an interventional device, including:
      a proximal grasping assembly movable between a pre-deployed position and a deployed position;
      a distal grasping assembly movable between a pre-deployed position and a deployed position, the distal grasping assembly being spaced apart from the proximal grasping assembly so as to define a grasping space therebetween for grasping tricuspid valve leaflets when the proximal grasping assembly and the distal grasping assembly are in deployed positions and are deployed at a tricuspid valve; and
      an actuator rod mounted operatively connected to each of the proximal grasping assembly and the distal grasping assembly so that distal movement of the actuator rod simultaneously moves the proximal grasping assembly proximally and the distal grasping assembly distally,
   wherein the sheath is configured to be retractable relative to the delivery catheter to expose the interventional device and enable the distal grasping assembly and the proximal grasping assembly to move toward the deployed configuration.

19. The interventional system of claim 18, wherein the distal grasping assembly comprises a first distal arm and a second distal arm, each being pivotally mounted to a central shaft receiving the actuator rod, and the proximal grasping assembly comprises a first proximal arm and a second proximal arm, each being pivotally mounted to the central shaft receiving the actuator rod.

20. The interventional system of claim 19, wherein distal advancement of the actuator rod rotates the first proximal arm and the second proximal arm proximally and rotates the first distal arm and the second distal arm distally.

* * * * *